(12) United States Patent
Braig et al.

(10) Patent No.: US 6,403,826 B1
(45) Date of Patent: Jun. 11, 2002

(54) CORROSION-INHIBITING COATING COMPOSITION FOR METALS

(75) Inventors: Adalbert Braig, Binzen (DE); Andreas Kramer, Düdingen (CH); Jean-Pierre Wolf, Courtaman (CH); Markus Frey, Marly (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/658,922

(22) Filed: Sep. 11, 2000

Related U.S. Application Data

(62) Division of application No. 09/363,556, filed on Jul. 29, 1999, now Pat. No. 6,160,164, which is a division of application No. 08/798,014, filed on Feb. 12, 1997, now Pat. No. 5,980,619.

(30) Foreign Application Priority Data

Feb. 12, 1996 (CH) .................................... 360/96
Apr. 12, 1996 (CH) .................................... 930/96

(51) Int. Cl.$^7$ .................................... C07F 9/38
(52) U.S. Cl. .................. 562/12; 544/106; 544/107; 544/110; 558/151; 558/152; 558/155; 562/11; 564/305
(58) Field of Search ...................... 562/12, 11; 558/151, 558/152, 155; 544/106, 107, 110; 564/305

(56) References Cited

U.S. PATENT DOCUMENTS

| | | | |
|---|---|---|---|
| 3,359,266 A | 12/1967 | Maier .......................... | 260/246 |
| 3,483,133 A | 12/1969 | Hatch et al. ................. | 252/389 |
| 3,629,124 A | 12/1971 | King .......................... | 252/99 |
| 3,837,803 A | 9/1974 | Carter et al. .................. | 21/2.7 |
| 3,925,245 A | 12/1975 | Harris et al. ................. | 252/389 |
| 4,000,012 A | 12/1976 | Burrows et al. ....... | 148/6.15 R |
| 4,033,896 A | 7/1977 | Mitchell et al. ............. | 252/389 |
| 4,076,501 A | 2/1978 | Harris et al. ................ | 21/2.7 A |
| 4,201,593 A | 5/1980 | Sienkowski et al. ..... | 106/18.21 |
| 4,298,723 A | 11/1981 | DiGiacomo et al. ........ | 528/271 |
| 4,330,487 A | 5/1982 | Redmore et al. ......... | 260/502.5 |
| 4,814,209 A | 3/1989 | Arnold ........................ | 427/409 |
| 4,909,987 A | 3/1990 | Penninger et al. ............. | 422/17 |
| 4,917,737 A | 4/1990 | Carey et al. ................. | 148/250 |
| 5,458,678 A | 10/1995 | Armstrong et al. ...... | 106/14.41 |

FOREIGN PATENT DOCUMENTS

| | | |
|---|---|---|
| DE | 2231206 | 12/1972 |
| DE | 2335331 | 2/1974 |
| EP | 0199702 | 10/1986 |
| EP | 0412933 | 2/1991 |
| EP | 0437722 | 7/1991 |
| EP | 0496555 | 7/1992 |
| EP | 0554023 | 8/1993 |
| EP | 0619290 | 10/1994 |
| GB | 1201334 | 8/1970 |
| GB | 2121419 | 12/1983 |

OTHER PUBLICATIONS

Speier et al., J. Org. Chem., vol. 36, (21), pp. 3120–3126 (1971).
Chem. Abstr. 88:105563f, 1978.
Chem. Abstr. 111:214572x, 1989.
K. Moedritzer et al., J. Org. Chem., vol. 31, pp. 1603–1607, (1966).
Müller et al, Methoden Der Organischen Chemie, Band XII/I, Seiten 483–489 (1963), Houben–Weyl.
Regitz et al., Methoden Der Organischen Chemie, Band E2, pp. 302–304, (1982), Houbon–Weyl.

*Primary Examiner*—Shailendra Kumar
(74) *Attorney, Agent, or Firm*—Kevin T. Mansfield

(57) ABSTRACT

A description is given of compounds of the formula

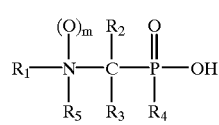

(I)

in which the general symbols are as defined in claim 1, and of their zirconium, bismuth and calcium salts, and of the salts with the compounds of the formula II

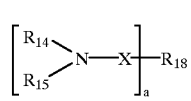

(II)

in which the general symbols are as defined in claim 1, as corrosion inhibitors in coating compositions for protecting metallic surfaces.

3 Claims, No Drawings

CORROSION-INHIBITING COATING COMPOSITION FOR METALS

This is a divisional of application Ser. No. 09/363,556, filed on Jul. 29, 1999, now U.S. Pat. No. 6,160,164, which is a divisional of application Ser. No. 08/798,014, filed Feb. 12, 1997, now U.S. Pat. No. 5,980,619.

The present invention relates to coating compositions comprising an organic film-forming binder, preferably a coating material, and certain aminophosphonic acids or aminophosphorous acids and/or their zirconium, bismuth and calcium salts, and salts thereof with certain amines, as corrosion inhibitors, to the use thereof in coating compositions for protecting metallic surfaces, and to novel aminophosphonic acids and novel salts of aminophosphonic acids and of aminophosphorous acids.

The use of alkali metal, alkaline earth metal, transition metal and amine salts of carboxylic acids, and of transition metal complexes of ketocarboxylic acids, as corrosion inhibitors in aqueous systems is known and is described, for example, in U.S. Pat. No. 4,909,987, EP-A-0 412 933, EP-A-0 496 555, EP-A-0 554 023 or EP-A-0 619 290.

EP-A-0 437 722 discloses certain amine oxides of phosphonic acids as corrosion inhibitors. U.S. Pat. No. 4,000,012 describes an anticorrosion effect of iron phosphate or zinc phosphate coatings on steel, the action of which is markedly improved by treatment with a solution of an α-aminophosphonic acid or water-soluble salts thereof. U.S. Pat. No. 4,076,501 refers to an anticorrosion effect of metals by means of diphosphonic acids. U.S. Pat. No. 4,917,737 describes a method of sealing off a phosphated metal substrate using certain alkylaminodiphosphonic acids. U.S. Pat. No. 3,925,245 (DE-A-2 231 206) refers to a corrosion-inhibiting composition for metal surfaces, comprising inorganic nitrites and aminoalkylphosphonic acids. U.S. Pat. No. 3,837,803 (DE-A-2 335 331) relates to a process of corrosion inhibition for metallic components which are in contact with aqueous systems, through the use of synergistic mixtures of water-soluble organophosphonic acids and their salts, a water-soluble orthophosphate, and calcium ions. U.S. Pat. No. 3,483,133 relates to the use of certain aminomethylphosphonic acids as corrosion inhibitors for metals in aqueous systems. GB-A-1 201 334 likewise discloses the use of certain phosphonic acids as corrosion inhibitors for metals in aqueous systems.

GB-A-2 121 419 discloses the use of certain phosphonic acids as corrosion inhibitors in coating materials.

One of the objects of the invention, then, was to provide—specifically for coating systems, especially those which are water-based—a coating composition which, firstly, inhibits or eliminates entirely the corrosion of metals, and, secondly, promotes good adhesion of the coating to the metal.

It has been found that certain aminophosphonic acids or aminophosphorous acids and/or their zirconium, bismuth and calcium salts, and also the salts thereof with certain amines, surprisingly suppress the oxidation of metals, and at the same time they greatly improve the adhesion of the coating to the metal. These acids and salts are for the most part novel, and are particularly suitable in the novel coating compositions both as corrosion inhibitors and as adhesion promoters.

The invention therefore relates to coating compositions comprising
a) an organic film-forming binder, and
b) as corrosion inhibitor α) at least one compound of the formula I

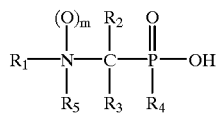

(I)

in which
$R_1$ is hydroxyl-, carboxyl- or amino-substituted $C_4$–$C_{12}$alkyl; or $R_1$ and $R_5$, together with the nitrogen atom to which they are attached, form a 5-, 6- or 7-membered heterocyclic ring which is unsubstituted or is substituted by $C_1$–$C_4$alkyl or is interrupted by oxygen, sulfur or

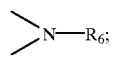

$R_2$ and $R_3$ independently of one another are hydrogen, $C_1$–$C_{20}$alkyl, $C_5$–$C_8$cycloalkyl, unsubstituted or $C_1$–$C_4$alkyl-substituted phenyl; or are benzyl,
$R_4$ is hydroxyl,
$R_5$ is

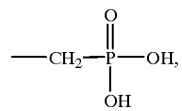

$R_6$ is $C_1$–$C_{18}$alkyl or $C_7$–$C_9$phenylalkyl, and
m is 0 or 1; or
β) at least one salt derived from i) a compound of the formula I'

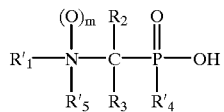

(I')

in which
$R'_1$ is hydrogen, $C_1$–$C_{25}$alkyl, $C_3$–$C_{25}$alkyl interrupted by oxygen, sulfur or

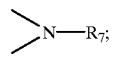

hydroxyl-, carboxyl- or amino-substituted $C_2$–$C_{25}$alkyl; $C_2$–$C_{24}$alkenyl, $C_4$–$C_{15}$cycloalkyl, unsubstituted or $C_1$–$C_4$alkyl-substituted phenyl; $C_7$–$C_9$phenylalkyl or

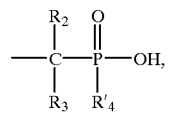

or $R'_1$ and $R'_5$, together with the nitrogen atom to which they are attached, form a 5-, 6- or 7-membered heterocyclic ring which is unsubstituted or is substituted by $C_1$–$C_4$alkyl or is interrupted by oxygen, sulfur or

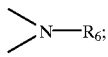

$R'_4$ is hydrogen, hydroxyl or —$OR_8$,
$R'_5$ is hydrogen, $C_1$–$C_{25}$alkyl, $C_3$–$C_{25}$alkyl interrupted by oxygen, sulfur or

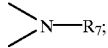

$C_2$–$C_{24}$alkenyl, $C_4$–$C_{15}$cycloalkyl, unsubstituted or $C_1$–$C_4$alkyl-substituted phenyl; $C_7$–$C_9$-phenylalkyl or

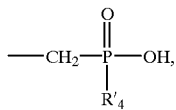

$R_7$ is hydrogen or $C_1$–$C_6$alkyl,
$R_8$ is $C_1$–$C_6$alkyl, $C_4$–$C_{15}$cycloalkyl or unsubstituted or $C_1$–$C_4$alkyl-substituted phenyl; with the proviso that, if $R'_1$ or $R'_5$ is hydrogen, m is 0; and ii) an amine of the formula II

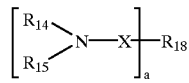

(II)

in which
$R_{14}$ and $R_{15}$ independently of one another are hydrogen, $C_1$–$C_{25}$alkyl, hydroxyl-substituted $C_2$–$C_{24}$alkyl, $C_3$–$C_{25}$alkyl interrupted by oxygen or sulfur; $C_7$–$C_9$-phenylalkyl which is unsubstituted or is substituted on the phenyl ring by $C_1$–$C_4$alkyl; $C_3$–$C_{24}$alkenyl or

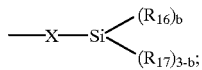

or $R_{14}$ and $R_{15}$, together with the nitrogen atom to which they are attached, form a 5-, 6- or 7-membered heterocyclic ring which is unsubstituted or is substituted by $C_1$–$C_4$alkyl or is interrupted by oxygen, sulfur or

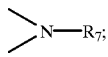

$R_{16}$ is $C_1$–$C_{25}$alkyl, $C_2$–$C_{25}$alkyl which is interrupted by oxygen or sulfur; hydroxyl, $C_1$–$C_{18}$alkoxy or $C_2$–$C_{24}$alkenyl,
$R_{17}$ is hydroxyl, $C_1$–$C_{18}$alkoxy, or $C_2$–$C_{18}$alkoxy which is interrupted by oxygen or sulfur; and, if b is 0, three radicals $R_{17}$ together are $N(CH_2CH_2O—)_3$,
X is a direct bond, $C_1$–$C_{18}$alkylene, $C_2$–$C_{20}$alkylidene, $C_7$–$C_{20}$ phenylalkylidene, $C_5$–$C_8$cycloalkylene, unsubstituted or $C_1$–$C_4$alkyl substituted phenylene or naphthylene;

or is $C_4$–$C_{18}$alkylene which is interrupted by oxygen, sulfur or

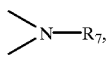

with the proviso that never two nitrogen atoms are attached to the same carbon atom,
a is 1 or 2,
b is 0, 1 or 2, and,
if a is 1,
$R_{18}$ is hydrogen, $C_1$–$C_{25}$alkyl, hydroxyl-substituted $C_2$–$C_{24}$alkyl, $C_3$–$C_{25}$alkyl which is interrupted by oxygen or sulfur; unsubstituted or $C_1$–$C_4$alkyl-substituted phenyl; $C_7$–$C_9$-phenylalkyl which is unsubstituted or is substituted on the phenyl ring by $C_1$–$C_4$alkyl; $C_3$–$C_{24}$alkenyl,

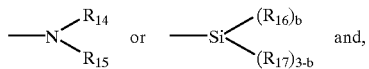

if a is 2,
$R_{18}$ is

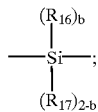

and with the proviso that, if in the compound of the formula I' $R'_1$ is $C_1$–$C_{12}$alkyl,

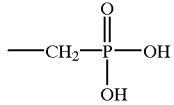

or 2-hydroxyethyl, $R'_5$ is

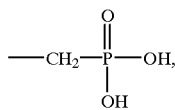

$R_2$ and $R_3$ are hydrogen, $R'_4$ is hydroxyl and m is 0, and, if in the compound of the formula II a is 1 and X is a direct bond, then at least one of the radicals $R_{14}$, $R_{15}$ and $R_{18}$ is other than hydrogen; or iii) zirconium, bismuth or calcium.

Hydroxyl-, carboxyl- or amino-substituted $C_2$–$C_2$alkyl is a branched or unbranched radical which contains preferably 1 to 3, in particular 1 or 2, hydroxyl, carboxyl or amino groups, such as, for example, hydroxyethyl, carboxyethyl, aminoethyl, 3-hydroxypropyl, 3-carboxypropyl, 3-aminopropyl, 2-hydroxypropyl, 2-carboxypropyl, 2-aminopropyl, 4-hydroxybutyl, 4-carboxybutyl, 4-aminobutyl, 3-hydroxybutyl, 3-carboxybutyl, 3-aminobutyl, 2-hydroxybutyl, 2-carboxybutyl, 2-aminobutyl, 5-hydroxypentyl, 5-carboxypentyl, 5-aminopentyl, 4-hydroxypentyl, 4-carboxypentyl, 4-aminopentyl, 3-hydroxypentyl, 3-carboxypentyl, 3-aminopentyl, 2-hydroxypentyl, 2-carboxypentyl, 2-aminopentyl, 6-hydroxyhexyl, 6-carboxyhexyl, 6-aminohexyl, 5-hydroxyhexyl, 5-carboxyhexyl, 5-aminohexyl, 4-hydroxyhexyl, 4-carboxyhexyl, 4-aminohexyl, 3-hydroxyhexyl, 3-carboxyhexyl, 3-aminohexyl, 2-hydroxyhexyl, 2-carboxyhexyl, 2-aminohexyl, 7-hydroxyheptyl, 7-carboxyheptyl, 7-aminoheptyl, 6-hydroxyheptyl, 6-carboxyheptyl, 6-aminoheptyl, 5-hydroxyheptyl, 5-carboxyheptyl, 5-aminoheptyl, 4-hydroxyheptyl, 4-carboxyheptyl, 4-aminoheptyl, 3-hydroxyheptyl, 3-carboxyheptyl, 3-aminoheptyl, 2-hydroxyheptyl, 2-carboxyheptyl, 2-aminoheptyl, 8-hydroxyoctyl, 8-carboxyoctyl, 8-aminooctyl, 7-hydroxyoctyl, 7-carboxyoctyl, 7-aminooctyl, 6-hydroxyoctyl, 6-carboxyoctyl, 6-aminooctyl, 5-hydroxyoctyl, 5-carboxyoctyl, 5-aminooctyl, 4-hydroxyoctyl, 4-carboxyoctyl, 4-aminooctyl, 3-hydroxyoctyl, 3-carboxyoctyl, 3-aminooctyl, 2-hydroxyoctyl, 2-carboxyoctyl, 2-aminooctyl, 9-hydroxynonyl, 9-carboxynonyl, 9-aminononyl, 10-hydroxydecyl, 10-carboxydecyl, 10-aminodecyl, 11-hydroxyundecyl, 11-carboxyundecyl, 11-aminoundecyl, 12-hydroxydodecyl, 12-carboxydodecyl, 12-aminododecyl, 13-hydroxytridecyl, 13-carboxytridecyl, 13-aminotridecyl, 14-hydroxytetradecyl, 14-carboxytetradecyl, 14-aminotetradecyl, 15-hydroxypentadecyl, 15-carboxypentadecyl, 15-aminopentadecyl, 16-hydroxyhexadecyl, 16-carboxyhexadecyl, 16-aminohexadecyl, 17-hydroxyheptadecyl, 17-carboxyheptadecyl, 17-aminoheptadecyl, 18-hydroxyoctadecyl, 18-carboxyoctadecyl, 18-aminooctadecyl, 20-hydroxyeicosyl, 20-carboxyeicosyl, 20-aminoeicosyl, 22-hydroxydocosyl, 22-carboxyeicosyl or 22-aminoeicosyl. A preferred definition of $R_1$ is hydroxyl-, carboxyl- or amino-substituted $C_4$–$C_{12}$alkyl, especially hydroxyl- or carboxyl-substituted $C_5$–$C_{12}$alkyl, for example hydroxyl- or carboxyl-substituted $C_5$–$C_{11}$alkyl. A particularly preferred definition of $R_1$ is hydroxyl- or carboxyl-substituted $C_5$–$C_{10}$alkyl, especially hydroxyl- or carboxyl-substituted $C_5$–$C_8$alkyl, for example hydroxyl-substituted $C_5$–$C_6$alkyl. An especially preferred definition of $R_1$ is 5-hydroxypentyl. A preferred definition of $R'_1$ is hydroxyl-, carboxyl- or amino-substituted $C_2$–$C_{20}$alkyl, especially hydroxyl-, carboxyl- or amino-substituted $C_5$–$C_{20}$alkyl, for example hydroxyl-, carboxyl- or amino-substituted $C_5$–$C_{12}$alkyl. A particularly preferred definition of $R'_1$ is hydroxyl- or carboxyl-substituted $C_5$–$C_{12}$alkyl, especially hydroxyl- or carboxyl-substituted $C_5$–$C_{11}$alkyl, for example 5-hydroxypentyl or 11-carboxyundecyl. A particularly preferred definition of $R''_1$ is hydroxyl-, carboxyl- or amino-substituted $C_4$–$C_{14}$alkyl, especially hydroxyl- or carboxyl-substituted $C_5$–$C_{14}$alkyl, for example hydroxyl- or carboxyl-substituted $C_5$–$C_{11}$alkyl. One of the preferred definitions of $R_{14}$, $R_{15}$ and $R_{18}$ (if a=1) is hydroxyl-substituted $C_2$–$C_{24}$alkyl, especially hydroxyl-substituted $C_2$–$C_{20}$alkyl, for example hydroxyl-substituted $C_2$–$C_{14}$alkyl. A particularly preferred definition of $R_{14}$, $R_{15}$ and $R_{18}$ is hydroxyl-substituted $C_2$–$C_{12}$alkyl, especially hydroxyl-substituted $C_2$–$C_8$alkyl, for example hydroxyl-substituted $C_2$–$C_4$alkyl, such as 2-hydroxyethyl, for example.

Where $R_1$ and $R_5$ or $R'_1$ and $R'_5$ or $R''_1$ and $R''_5$ or $R_{14}$ and $R_{15}$, together with the nitrogen atom to which they are attached, form a 5-, 6- or 7-membered heterocyclic ring which is unsubstituted or is substituted by $C_1$–$C_4$alkyl or is interrupted by oxygen, sulfur or

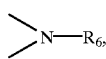

this denotes, for example, the following radicals:

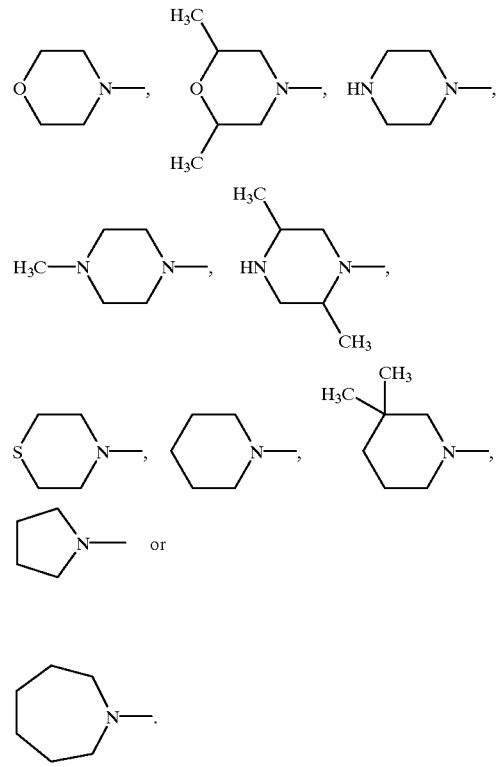

$R_{14}$ and $R_{15}$ preferably form, with the nitrogen atom to which they are attached, a 6-membered heterocyclic ring interrupted by oxygen, such as, for example,

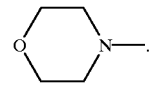

Alkyl having up to 25 carbon atoms is a branched or unbranched radical such as, for example, methyl, ethyl, propyl, isopropyl, n-butyl, sec-butyl, isobutyl, tert-butyl, 2-ethyl-butyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred definition of $R_2$ and $R_3$ is $C_1$–$C_{20}$alkyl, especially $C_1$–$C_{12}$alkyl, for example $C_1$–$C_8$alkyl. A particularly preferred definition of $R_2$ and $R_3$ is $C_1$–$C_6$alkyl, especially $C_1$–$C_4$alkyl, for example methyl. A preferred definition of $R_6$ is $C_1$–$C_{18}$-alkyl, especially $C_1$–$C_{12}$alkyl, for example $C_1$–$C_8$alkyl. A particularly preferred definition of $R_6$ is $C_1$–$C_6$alkyl, especially $C_1$–$C_4$alkyl, for example methyl or ethyl. A preferred definition of $R'_1$ and $R'_5$ is $C_1$–$C_{25}$alkyl, especially $C_5$–$C_{20}$alkyl, for example $C_5$–$C_{18}$alkyl. A preferred definition of $R''_1$ and $R''_5$ is $C_8$–$C_{14}$alkyl. A preferred definition of $R_7$ is $C_1$–$C_6$alkyl, especially $C_1$–$C_4$alkyl, for example methyl. A preferred definition of $R_8$ is $C_1$–$C_6$alkyl, especially $C_1$–$C_4$alkyl, for example methyl or ethyl. A preferred definition of $R_{14}$, $R_{15}$, $R_{16}$ and $R_{18}$ is $C_1$–$C_{20}$alkyl, especially $C_1$–$C_{14}$alkyl, for example $C_1$–$C_{12}$alkyl. A particularly preferred definition of $R_{14}$, $R_{15}$, $R_{16}$ and $R_{18}$ is $C_1$–$C_8$alkyl, especially $C_1$–$C_4$alkyl, for example methyl or ethyl.

$C_4$–$C_{15}$cycloalkyl is, for example, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl or cyclopentadecyl. A preferred definition of $R'_1$, $R_2$, $R_3$, $R'_5$ and $R_8$ is $C_5$–$C_8$cycloalkyl, especially $C_6$–$C_7$cycloalkyl, for example cyclohexyl.

$C_1$–$C_4$alkyl substituted phenyl which preferably contains 1 to 3, in particular 1 or 2, alkyl groups, is, for example, o-, m- or p-methylphenyl, 2,3-dimethylphenyl, 2,4-dimethylphenyl, 2,5dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$–$C_9$phenylalkyl which is unsubstituted or is substituted on the phenyl radical by from 1 to 3 $C_1$–$C_4$alkyl is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_3$–$C_{25}$alkyl which is interrupted by oxygen, sulfur or

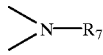

is, for example, $CH_3$—O—$CH_2CH_2$—, $CH_3$—S—$CH_2CH_2$—, $CH_3$—$NHCH_2CH_2$—, $CH_3$—$N(CH_3)CH_2CH_2$—, $CH_3$—O—$CH_2CH_2$—O—$CH_2CH_2$—, $CH_3$—(O—$CH_2CH_2$—)$_2$O—$CH_2CH_2$—, $CH_3$—(O—$CH_2CH_2$—)$_3$O—$CH_2CH_2$— or $CH_3$—(O—$CH_2CH_2$—)$_4$O—$CH_2$—.

Alkenyl having 2 to 24 carbon atoms is a branched or unbranched radical such as, for example, vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n4octadecenyl. Preference is given to alkenyl having 3 to 18, especially 3 to 12, for example 3 to 6, especially 3 to 4 carbon atoms.

Alkoxy having up to 18 carbon atoms is a branched or unbranched radical such as, for example, methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having 1 to 12, especially 1 to 8, for example 1 to 6, carbon atoms.

Oxygen- or sulfur-interrupted $C_2$–$C_{18}$-alkoxy is, for example, $CH_3$—O—$CH_2$—, $CH_3$—S—$CH_2$—, $CH_3$—O—$CH_2CH_2O$—, $CH_3$—S—$CH_2CH_2O$—, $CH_3$—O—$(CH_2)_2$—O—$(CH_2)_2$—O—, $CH_3$—(O—$CH_2CH_2$—)$_2$O—$CH_2CH_2O$—, $CH_3$—(O—$CH_2CH_2$—)$_3$O—$CH_2CH_2O$— or $CH_3$—(O—$CH_2CH_2$—)$_4$O—$CH_2CH_2O$—.

$C_1$–$C_{18}$-alkylene is a branched or unbranched radical such as, for example, methylene, ethylene, propylene, trimethylene, tetramethylene, pentamethylene, hexamethylene, heptamethylene, octamethylene, decamethylene, dodecamethylene or octadecamethylene. Preference is given to $C_1$–$C_{12}$alkylene, especially $C_1$–$C_8$alkylene.

Alkylidene having 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. $C_2$–$C_8$-alkylidene is preferred.

Phenylalkylidene having 7 to 20 carbon atoms is, for example, benzylidene, 2-phenylethylidene or 1-phenyl-2-heptylidene. $C_7$–$C_9$phenylalkylidene is preferred.

$C_5$–$C_8$cycloalkylene is a saturated hydrocarbon group having two free valencies and at least one ring unit and is, for example, cyclopentylene, cyclohexylene, cycloheptylene or cyclooctylene. Cyclohexylene is preferred.

Unsubstituted or $C_1$–$C_4$alkyl-substituted phenylene or naphthylene is, for example, 1,2-, 1,3- or 1,4-phenylene, or 1,2-, 1,3-, 1,4-, 1,6-, 1,7-, 2,6- or 2,7-naphthylene. 1,4-Phenylene preferred.

$C_4$–$C_{18}$-alkylene which is interrupted by oxygen, sulfur or

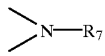

is, for example, —$CH_2CH_2$—O—$CH_2CH_2$—, —$CH_2CH_2$—S—$CH_2CH_2$—, —$CH_2CH_2$—NH—$CH_2CH_2$—, —$CH_2CH_2$—N($CH_3$)—$CH_2CH_2$—, —$CH_2CH_2$—O—$CH_2CH_2$—O—$CH_2CH_2$—, —$(CH_2)_2$—(O—$CH_2CH_2$—)$_2$O—$(CH_2)_2$—, —$(CH_2)_2$—(O—$CH_2CH_2$—)$_3$O—$(CH_2)_2$—, —$(CH_2)_2$—(O—$CH_2CH_2$—)$_4$O—$(CH_2)_2$— or —$CH_2CH_2$—S—$CH_2CH_2$—.

Particular mention is to be made of coating compositions comprising as component (b) at least one compound of the formula I or a salt derived from i) a compound of the formula I' and ii) an amine of the formula II, in which $R_2$ and $R_3$ are hydrogen.

Advantageous coating compositions are those comprising as component (b) at least one compound of the formula I in which $R_1$ is hydroxyl- or carboxyl-substituted $C_5$–$C_{12}$alkyl.

Preference is given to coating compositions comprising as component (b) at least one salt derived from i) a compound of the formula I' and ii) an amine of the formula II in which $R'_1$ is $C_5$–$C_{18}$alkyl, or hydroxyl- or carboxyl-substituted $C_5$–$C_{12}$alkyl;

$R'_4$ is hydrogen or hydroxyl, and $R'_5$ is $C_5$–$C_{25}$alkyl or

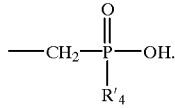

Preference is also given to coating compositions comprising as component (b) at least one salt derived from i) a compound of formula I' and ii) an amine of the formula II in which $R_{14}$ and $R_{15}$ independently of one another are hydrogen, $C_1$–$C_8$alkyl, or hydroxyl-substituted $C_2$–$C_{14}$alkyl; or $R_{14}$ and $R_{15}$, together with the nitrogen atom to which they are attached, form an oxygen-interrupted 6-membered heterocyclic ring, X is a direct bond, a is 1, and $R_{18}$ is $C_1$–$C_{14}$alkyl, hydroxyl-substituted $C_2$–$C_{14}$alkyl; unsubstituted or $C_1$–$C_4$alkyl-substituted phenyl; or is benzyl.

Also of interest are coating compositions comprising as component (b) at least one compound of the formula I or a salt derived from i) a compound of the formula I' and ii) an amine of the formula II in which $R_1$ is hydroxyl-, carboxyl- or amino-substituted $C_5$–$C_{12}$alkyl; or $R_1$ and $R_5$, together with the nitrogen atom to which they are attached, form a 5-, 6- or 7-membered heterocyclic ring which is interrupted by oxygen, sulfur or

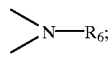

$R'_1$ is $C_5$–$C_{20}$alkyl, $C_5$–$C_{20}$alkyl which is interrupted by oxygen, sulfur or

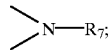

hydroxyl-, carboxyl- or amino-substituted $C_5$–$C_{20}$alkyl; $C_5$–$C_{20}$alkenyl, $C_5$–$C_8$cycloalkyl, unsubstituted or $C_1$–$C_4$alkyl-substituted phenyl; benzyl or

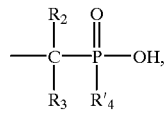

or $R'_1$ and $R'_5$, together with the nitrogen atom to which they are attached, form a 6-membered heterocyclic ring which is unsubstituted or is substituted by $C_1$–$C_4$alkyl or is interrupted by oxygen, sulfur or

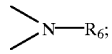

$R_2$ and $R_3$ independently of one another are hydrogen, $C_1$–$C_{12}$alkyl, $C_5$–$C_7$cycloalkyl, phenyl or benzyl;
$R_4$ is hydroxyl,
$R'_4$ is hydrogen, hydroxyl or —$OR_8$,
$R_5$ is

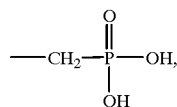

$R'_5$ is hydrogen, $C_5$–$C_{20}$alkyl, $C_5$–$C_{20}$alkyl which is interrupted by oxygen, sulfur or

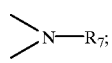

$C_5$–$C_{20}$alkenyl, $C_5$–$C_8$cycloalkyl, unsubstituted or $C_1$–$C_4$alkyl-substituted phenyl; benzyl or

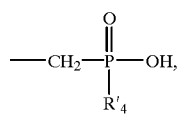

$R_6$ is $C_1$–$C_{12}$alkyl or benzyl,
m is 0 or 1, $R_7$ is hydrogen or $C_1$–$C_6$alkyl,
$R_8$ is $C_1$–$C_6$alkyl, cyclohexyl or phenyl,
$R_{14}$ and $R_{15}$ independently of one another are hydrogen, $C_1$–$C_{20}$alkyl, hydroxyl-substituted $C_2$–$C_{20}$alkyl, oxygen- or sulfur-interrupted $C_3$–$C_{20}$alkyl; $C_7$–$C_9$phenylalkyl; $C_3$–$C_{20}$alkenyl or

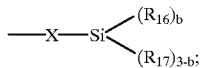

or $R_{14}$ and $R_{15}$, together with the nitrogen atom to which they are attached, form a 6-membered heterocyclic ring which is interrupted by oxygen, sulfur or

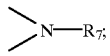

$R_{16}$ is $C_1$–$C_{20}$alkyl, oxygen- or sulfur-interrupted $C_2$–$C_{20}$alkyl; hydroxyl, $C_1$–$C_{12}$alkoxy or $C_2$–$C_{20}$alkenyl,
$R_{17}$ is hydroxyl, $C_1$–$C_{12}$alkoxy, or oxygen- or sulfur-interrupted $C_2$–$C_{12}$alkoxy; and, if b is 0, three radicals $R_{17}$ together are $N(CH_2CH_2O—)_3$,
X is a direct bond, $C_1$–$C_{12}$alkylene, $C_2$–$C_{12}$alkylidene, $C_7$–$C_{12}$phenylalkylidene, $C_5$–$C_8$cyclohexylene, phenylene, naphthylene, or oxygen- or sulfur-interrupted $C_4$–$C_{18}$alkylene, with the proviso that never two nitrogen atoms are attached to the same carbon atom,
a is 1 or 2,
b is 0, 1 or 2, and,
if a is 1,
$R_{18}$ is hydrogen, $C_1$–$C_{20}$alkyl, hydroxyl-substituted $C_2$–$C_{20}$alkyl, oxygen- or sulfur-interrupted $C_3$–$C_{20}$alkyl; phenyl, $C_7$–$C_9$phenylalkyl, $C_3$–$C_{20}$alkenyl,

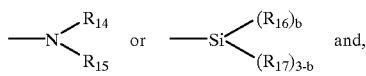

if a is 2,
$R_{18}$ is

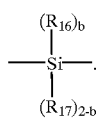

There is particular interest in coating compositions comprising as component (b) at least one compound of the formula I or a salt derived from i) a compound of the formula I' and ii) an amine of the formula II in which
$R_1$ is hydroxyl- or carboxyl-substituted $C_5$–$C_{11}$alkyl; or $R_1$ and $R_5$, together with the nitrogen atom to which they are attached, form an oxygen- or sulfur-interrupted 6-membered heterocyclic ring;
$R'_1$ is $C_5$–$C_{20}$alkyl, oxygen- or sulfur-interrupted $C_5$–$C_{20}$alkyl; hydroxyl- or carboxyl-substituted $C_5$–$C_{11}$alkyl; $C_5$–$C_{10}$alkenyl, cyclohexyl, phenyl or benzyl, or $R'_1$ and $R'_5$, together with the nitrogen atom to which they are attached, form an oxygen- or sulfur-interrupted 6-membered heterocyclic ring;

$R_2$ and $R_3$ independently of one another are hydrogen, $C_1$–$C_4$alkyl, cyclohexyl, phenyl or benzyl, $R_4$ is hydroxyl, $R'_4$ is hydrogen or hydroxyl, $R_5$ is

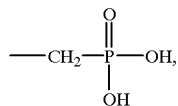

$R'_5$ is $C_5$–$C_{20}$alkyl, oxygen- or sulfur-interrupted $C_5$–$C_{20}$alkyl; $C_5$–$C_{20}$alkenyl, cyclohexyl, phenyl, benzyl or

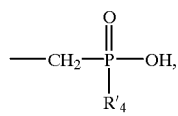

m is 0, $R_{14}$ and $R_{15}$ independently of one another are hydrogen, $C_1$–$C_{12}$alkyl, hydroxyl-substituted $C_2$–$C_{12}$alkyl, oxygen- or sulfur-interrupted $C_3$–$C_{12}$alkyl; benzyl, $C_3$–$C_{12}$alkenyl or

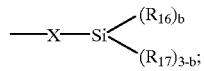

or $R_{14}$ and $R_{15}$, together with the nitrogen atom to which they are attached, form an oxygen- or sulfur-interrupted 6-membered heterocyclic ring;

$R_{16}$ is $C_1$–$C_{12}$alkyl, oxygen- or sulfur-interrupted $C_2$–$C_{12}$alkyl; hydroxyl, $C_1$–$C_{12}$alkoxy or $C_2$–$C_{12}$alkenyl, $R_{17}$ is hydroxyl or $C_1$–$C_{12}$alkoxy; and, if b is 0, three radicals $R_{17}$ together are $N(CH_2CH_2O-)_3$, X is a direct bond, $C_1$–$C_8$alkylene, cyclohexylene, phenylene, naphthylene, or is oxygen-interrupted $C_4$–$C_{12}$alkylene, with the proviso that never two nitrogen atoms are attached to the same carbon atom, a is 1 or 2, b is 0, 1 or 2, and, if a is 1,
$R_{18}$ is hydrogen, $C_1$–$C_{12}$alkyl, hydroxyl-substituted $C_2$–$C_{12}$alkyl, oxygen-interrupted $C_3$–$C_{12}$alkyl; phenyl, benzyl, $C_3$–$C_{12}$alkenyl or

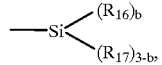

if a is 2,
$R_{18}$ is

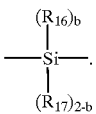

Coating compositions which are especially of particular interest are those comprising as component b) at least one compound of the formula I or a salt derived from i) a compound of the formula I' and ii) an amine of the formula II in which $R_1$ is hydroxyl- or carboxyl-substituted $C_5$–$C_{11}$alkyl, $R'_1$ is $C_5$–$C_{18}$alkyl, or hydroxyl- or carboxyl-substituted $C_5$–$C_{11}$alkyl;

$R_2$ is hydrogen, $R_3$ is hydrogen, $R_4$ is hydroxyl, $R'_4$ is hydrogen or hydroxyl, $R_5$ is

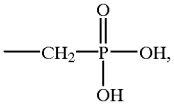

$R'_5$ is $C_5$–$C_{18}$alkyl or

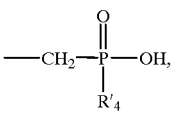

m is 0, $R_{14}$ and $R_{15}$ independently of one another are hydrogen, $C_1$–$C_4$alkyl, or hydroxyl-substituted $C_2$–$C_4$alkyl; or $R_{14}$ and $R_{15}$, together with the nitrogen atom to which they are attached, form an oxygen-interrupted 6-membered heterocyclic ring, X is a direct bond, a is 1, and $R_{18}$ is $C_1$–$C_4$alkyl, hydroxyl-substituted $C_2$–$C_4$alkyl; or is phenyl.

Examples of particularly preferred amines of the formula II are n-butylamine, isobutylamine, tert-butylamine, n-iso-/tert-amylamine, n-hexylamine, n-heptylamine, n-octylamine, isooctylamine, tert-octylamine, n-nonylamine, n-decylamine, n-dodecylamine, isododecylamine, tert-dodecylamine, n-tridecylamine, isotridecylamine, tert-tridodecylamine, n-tetradecylamine, isotetradecylamine, tert-tetradecylamine, n-octadecylamine, iso-octadecylamine, tert-octadecylamine, n-nonadecylamine, isononadecylamine, tert-nonadecylamine, n-eicosamine, iso-eicosamine, tert-eicosamine, n-heneicosamine, iso-heneicosamine, tert-heneicosamine, n-docosamine, iso-docosamine, tert-docosamine, n-tricosamine, isotricosamine, tert-tricosamin, n-tetracosamine, iso-tetracosamine, tert-tetracosamine, benzylamine, di-benzylamine, N-benzylaniline, di-n-butylamine, di-Isobutylamine, di-isodecylamine, di-tridodecylamine, di-isooctylamine, di-tert-octylamine, di-isotetradecylamine, di-n-octadecylamine, di-t- butylamine, di-n-octylamine, di-2-ethylhexylamine, di-n-dodecylamine, di-n-eicosylamine, di-n-tetraeicosylamine, 3-butoxypropylamine, hexoxybutylamine, nonyloxypropylamine, aniline, N-methylaniline, N-ethylaniline, N,N-dimethylaniline, tri-n-butylamine, triisobutylamine, tri-noctylamine and in particular, ethanolamine, N,N-dimethylaminoethanol, tris(hydroxymethyl)-aminomethane (TRISAMINO), 2-amino-2-ethyl-1,3-propanediol (AEPD), 2-amino-2-methyl-1-propanol (AMP 95), 2-dimethylamino-2-methyl-1-propanol (DMAMP 80), 2-amino-2-methyl-1,3-propanediol, N-methylmorpholine, N-ethylmorpholine, triethanolamine, triethfylamine, ammonia, 3-aminopropyltrimethoxysilane, N-methyl-3-aminopropyl-trimethoxysilane, 3-aminopropylmethyidiethoxysilane, 3-aminopropylmethyidiethoxysilane, N-alkyl-3-aminopropyltrimethoxysilane, 4-aminobutyltriethoxysilane, N,N'-dimethyl-3-aminopropyl-triethoxysilane, N,N'-dibutyl-3-aminopropyltrimethoxysilane, N,N'-(di-2-hydroxyethyl)-3-aminopropyltrimethoxysilane, bis-[3-(triethylsilyl)propyl]amine, 3-(2-aminoethylamino)propyl-trimethoxysilane, 3-(2-aminoethylamino)propylmethyldimethoxysilane, 3-(6-aminohexylamino)propyltrimethoxysilane, 3-[2-(2-aminoethylamino)ethylamino]propyltrimethoxysilane, aminophenyltrimethoxysilane and 3-aminopropyltrimethoxysilane. Particular preference is given to N-ethylmorpholine, N,N-dimethylaniline, triethanolamine, diethanolamine, triethylamine, ammonia, 3-aminopropyltrimethoxysilane and 3-aminopropyltrimethoxysilane.

Some of the compounds of the formula I and I' are known in the literature; others can be prepared in analogy to GB-A-2 121 419; K. Moedritzer et al., J. Org. Chem. 31, 1603–1607 (1966); Houben-Weyl, Methoden der Organischen Chemie [Methods of Organic Chemistry], volume XII/1, pages 483–489 (1963); or volume E2, 302–304 (1982).

The compounds of the formula II, especially the amino silanes, are known from the literature or can be prepared in analogy to J. L. Speier et al., J.Org. Chem. 36 (21), 3120–3126 (1971); L. Birkofer et al., Chapter 10, pages 655 to 751 in S. Palai, Z. Pappoport "The Chemistry of Organic Silicon Compounds", John Wiley & Sons Ltd., 1989; or E. P. Plueddeman, "Silane Coupling Agents", Plenum Press 1982, pages 1–233.

It is also possible to use mixtures of two or more different amines of the formula II for preparing the salts.

The salts derived from i) a compound of the formula I' and ii) an amine of the formula II or iii) zirconium, bismuth or calcium are expediently prepared in situ in the course of the formulation of the coating composition. The present invention therefore relates to coating compositions comprising (a') an organic film-forming binder, (b') at least one acid of the formula I', and (c') at least one amine of the formula II or a zirconium, bismuth or calcium compound.

The present invention also relates to a process for preparing a coating composition comprising as component (b) at least one compound of the formula I or a salt derived from i) a compound of the formula I' and ii) an amine of the formula II or iii) zirconium, bismuth or calcium, which comprises mixing an organic film-forming binder with the component (b).

The coating composition is preferably a coating material, especially an aqueous coating material.

Examples of coating materials are lacquers, paints or varnishes. These always contain an organic film-forming binder in addition to other, optional components.

Preferred organic film-forming binders are epoxy resins, polyurethane resins, amino resins, acrylic resins, acrylic copolymer resins, polyvinyl resins, phenolic resins, styrene/butadiene copolymer resins, vinyl/acrylic copolymer resins, polyester resins or alkyd resins, or a mixture of two or more of these resins, or an aqueous basic or acidic dispersion of these resins or mixtures of these resins, or an aqueous emulsion of these resins or mixtures of these resins.

Of particular interest are organic film-forming binders for aqueous coating compositions, such as, for example, alkyd resins; acrylic resins, two-component epoxy resins; polyurethane resins; polyester resins, which are usually saturated; water-dilutable phenolic resins or derived dispersions; water-dilutable urea resins; resins based on vinyl/acrylic copolymers; and hybrid systems based on, for example, epoxy acrylates.

More specifically, the alkyd resins can be water-dilutable alkyd resin systems which can be employed in air-drying form or in the form of stoving systems, optionally in combination with water-dilutable melamine resins; the systems may also be oxidatively drying, air-drying or stoving systems which are optionally employed in combination with aqueous dispersions based on acrylic resins or copolymers thereof, with vinyl acetates, etc.

The acrylic resins can be pure acrylic resins, epoxy acrylate hybrid systems, acrylic acid or acrylic ester copolymers, combinations with vinyl resins, or copolymers with vinyl monomers such as vinyl acetate, styrene or butadiene. These systems can be air-drying systems or stoving systems.

In combination with appropriate polyamine crosslinkers, water-dilutable epoxy resins exhibit excellent mechanical and chemical resistance. If liquid epoxy resins are used, the addition of organic solvents to aqueous systems can be omitted. The use of solid resins or solid-resin dispersions usually necessitates the addition of small amounts of solvent in order to improve film formation.

Preferred epoxy resins are those based on aromatic polyols, especially those based on bisphenols. The epoxy resins are employed in combination with crosslinkers. The latter may in particular be amino- or hydroxy-functional compounds, an acid, an acid anhydride or a Lewis acid. Examples thereof are polyamines, polyaminoamides, polysulfide-based polymers, polyphenols, boron fluorides and their complex compounds, polycarboxylic acids, 1,2-dicarboxylic anhydrides or pyromellitic dianhydride.

Polyurethane resins are derived from polyethers, polyesters and polybutadienes with terminal hydroxyl groups, on the one hand, and from aliphatic or aromatic polyisocyanates on the other hand.

Examples of suitable polyvinyl resins are polyvinylbutyral, polyvinyl acetate or copolymers thereof.

Suitable phenolic resins are synthetic resins in the course of whose construction phenols are the principal component, i.e. in particular phenol-, cresol-, xylenol- and resorcinol-formaldehyde resins, alkylphenolic resins, and condensation products of phenols with acetaldehyde, furfurol, acrolein or other aldehydes. Modified phenolic resins are also of interest.

The coating compositions may additionally comprise one or more components taken, for example, from the group consisting of pigments, dyes, fillers, flow control agents, dispersants, thixotropic agents, adhesion promoters, antioxidants, light stabilizers and curing catalysts. They may also include other known anticorrosion agents, for example anticorrosion pigments, such as phosphate- or borate-containing pigments or metal oxide pigments or other organic or inorganic corrosion inhibitors, for example salts of nitroisophthalic acid, phosphoric esters, technical-grade amines or substituted benzotriazoles.

The pigments are, for example, titanium dioxide, iron oxide, aluminum bronze or phthalocyanine blue.

Examples of fillers are talc, alumina, aluminum silicate, barytes, mica, and silica. The corrosion inhibitors can be applied to a support material. Pulverulent fillers or pigments are particularly suitable for this purpose.

Flow control agents and thixotropic agents are based, for example, on modified bentonites.

Adhesion promoters are based, for example, on modified silanes.

Also of advantage is the addition of basic fillers or pigments, which in particular binder systems give rise to a synergistic effect on corrosion inhibition. Examples of such basic fillers and pigments are calcium carbonate or magnesium carbonate, zinc oxide, zinc carbonate, zinc phosphate, magnesium oxide, alumina, aluminum phosphate or mixtures thereof. Examples of basic organic pigments are those based on aminoanthraquinone.

The corrosion inhibitors can be added to the coating material during its preparation, for example during pigment dispersion by grinding, or the inhibitor is dissolved in a solvent and the solution is then stirred into the coating composition. The solutions, especially aqueous solutions, of the corrosion inhibitors can also be used for pretreating the metal surface, which can then be subsequently coated with a topcoat.

In the preparation of the organic film-forming binder by addition polymerization or condensation polymerization of monomers, the corrosion inhibitors can be mixed in solid form, or dissolved, with the monomers even prior to the polymerization reaction.

The novel compounds of the formula I or salts derived from i) a compound of the formula I' and ii) an amine of the formula II or iii) zirconium, bismuth or calcium are expediently used in an amount of from 0.01 to 20% by weight, preferably from 0.05 to 5% by weight, in particular from 0.1 to 5% by weight, based on the weight of the overall solids content of the coating composition.

The coating materials can be applied to the substrate by the customary techniques, for example by spraying, dipping, spreading or electrodeposition. In many cases, a plurality of coats are applied. The corrosion inhibitors are added primarily to the base layer (primer), since they are active in particular at the metavcoating interface. However, they can also be added to the intermediate coat or topcoat, as well. Depending on whether the binder is a physically, chemically or oxidatively drying resin or a heat-curing or radiation-curing resin, the coating is cured at room temperature or by heating (stoving) or by irradiation.

The coating material is preferably a primer for metallic substrates such as, for example, iron, steel, copper, zinc or aluminum, and alloys thereof.

In addition to the anticorrosive effect, the compounds of the formula I or the salts derived from i) a compound of formula I' and ii) an amine of the formula II or iii) zirconium, bismuth or calcium have the advantage that they favourably affect the adhesion between coating and metal, show no adverse effects on the storage stability of the novel coating compositions, and exhibit good compatibility with the binder.

A preferred embodiment of the present invention is therefore the use of the compounds of the formula I or salts derived from i) compounds of the formula I' and ii) amines of the formula II or iii) zirconium, bismuth or calcium as corrosion inhibitors in coating compositions for metallic surfaces.

The present invention also relates to a process for protecting a corrodable metal substrate, which comprises applying thereto a coating composition comprising as component (a) an organic film-forming binder and as component (b) at least one compound of the formula I or at least one salt derived from i) a compound of the formula I' and ii) an amine of the formula II or iii) zirconium, bismuth or calcium, and then drying and/or curing the coating composition.

The present invention likewise relates to a process for preparing a corrosion-resistant surface coating on a corrodable metal surface, which comprises treating this surface with a coating composition comprising as component (a) an organic film-forming binder and as component (b) at least one compound of the formula I or at least one salt derived from i) a compound of the formula I' and ii) an amine of the formula II or iii) zirconium, bismuth or calcium, and then drying and/or curing the coating composition.

The present invention relates, moreover, to a process for pretreating metal surfaces, which comprises applying to the metal surface an aqueous solution of a component (b) comprising at least one compound of the formula I or at least one salt derived from i) a compound of the formula I' and ii) an amine of the formula II or iii) zirconium, bismuth or calcium, and drying it.

The invention further relates to novel compounds of the formula I

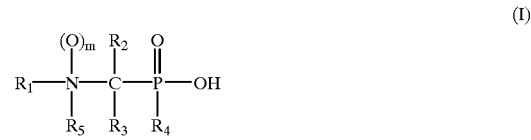

(I)

in which

R$_1$ is hydroxyl- or amino-substituted C$_4$–C$_{12}$alkyl; or R$_1$ and R$_5$, together with the nitrogen atom to which they are attached, are a 5-, 6- or 7-membered heterocyclic ring which is unsubstituted or is substituted by C$_1$–C$_4$alkyl or is interrupted by oxygen, sulfur or

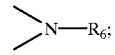

R$_2$ and R$_3$ independently of one another are hydrogen, C$_1$–C$_{20}$alkyl, C$_5$–C$_8$cycloalkyl, unsubstituted or C$_1$–C$_4$alkyl-substituted phenyl; or benzyl, R$_4$ is hydroxyl, R$_5$ is

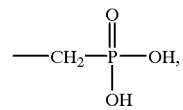

R$_6$ is C$_1$–C$_{18}$alkyl or C$_7$–C$_9$phenylalkyl, and m is 0 or 1; and with the proviso that the compound of the formula III

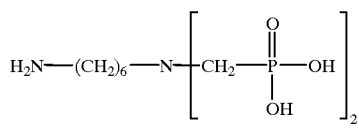 (III)

is excluded.

Preferred groups of novel compounds of the formula I correspond to the preferences expressed above for the coating compositions.

Preference is given, moreover, to compounds of the formula I in which $R_1$ is hydroxyl-substituted $C_5$–$C_{11}$alkyl; or $R_1$ and $R_5$, together with the nitrogen atom to which they are attached, form an oxygen- or sulfur-interrupted 6-membered heterocyclic ring;

$R_2$ and $R_3$ independently of one another are hydrogen, $C_1$–$C_4$alkyl, cyclohexyl, phenyl or benzyl, $R_4$ is hydroxyl, $R_5$ is

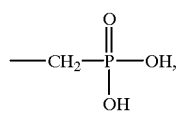

and m is 0.

Also of interest are compounds of the formula I in which $R_1$ is hydroxyl-substituted $C_5$–$C_8$alkyl, $R_2$ is hydrogen, $R_3$ is hydrogen, $R_4$ is hydroxyl, $R_5$ is

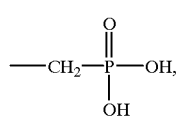

and m is 0.

The invention additionally relates to novel salts derived from i) a compound of the formula I″

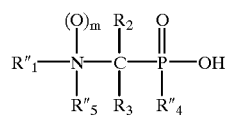 (I″)

in which $R''_1$ is $C_8$–$C_{14}$alkyl, hydroxyl-, carboxyl- or amino-substituted $C_4$–$C_{14}$alkyl; $C_8$–$C_{14}$ alkenyl or

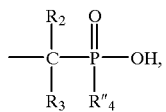

or $R''_1$ and $R''_5$, together with the nitrogen atom to which they are attached, form a 5-, 6- or 7-membered heterocyclic ring which is unsubstituted or substituted by $C_1$–$C_4$alkyl or is interrupted by oxygen, sulfur or

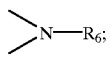

$R_2$ and $R_3$ independently of one another are hydrogen, $C_1$–$C_{20}$alkyl, $C_5$–$C_8$cycloalkyl, unsubstituted or $C_1$–$C_4$alkyl-substituted phenyl; or are benzyl, $R''_4$ is hydrogen or hydroxyl, $R''_5$ is hydrogen, $C_8$–$C_{14}$alkyl, $C_2$–$C_{24}$alkenyl or

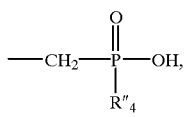

$R_6$ is $C_1$–$C_{18}$alkyl or $C_7$–$C_9$phenylalkyl, and m is 0 or 1; with the proviso that, if $R''_1$ or $R''_5$ is hydrogen, m is 0; and ii) an amine of the formula II

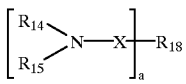 (II)

in which $R_{14}$ and $R_{15}$ independently of one another are hydrogen, $C_1$–$C_{25}$alkyl, hydroxyl-substituted $C_2$–$C_{24}$alkyl, oxygen- or sulfur-interrupted $C_3$–$C_{25}$alkyl; $C_7$–$C_9$phenylalkyl which is unsubstituted or is substituted on the phenyl ring by $C_1$–$C_4$alkyl; $C_3$–$C_{24}$alkenyl or

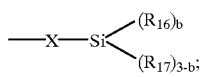

or $R_{14}$ and $R_{15}$, together with the nitrogen atom to which they are attached, form a 5-, 6- or 7-membered heterocyclic ring which is unsubstituted or is substituted by $C_1$–$C_4$alkyl or is interrupted by oxygen, sulfur or

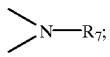

$R_7$ is hydrogen or $C_1$–$C_6$alkyl, $R_{16}$ is $C_1$–$C_{25}$alkyl, oxygen- or sulfur-interrupted $C_2$–$C_{25}$alkyl; hydroxyl, $C_1$–$C_{18}$alkoxy or $C_2$–$C_{24}$alkenyl, $R_{17}$ is hydroxyl, $C_1$–$C_{18}$alkoxy, or oxygen- or sulfur-interrupted $C_2$–$C_{18}$alkoxy; and, if b is 0, three radicals $R_{17}$ together are $N(CH_2CH_2O—)_3$, X is a direct bond, $C_1$–$C_{18}$alkylene, $C_2$–$C_{20}$alkylidene, $C_7$–$C_{20}$phenylalkylidene, $C_5$–$C_8$-cycloalkylene, unsubstituted or $C_1$–$C_4$alkyl-substituted phenylene or naphthylene; or
$C_4$–$C_{18}$alkylene which is interrupted by oxygen, sulfur or

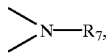

with the proviso that never two nitrogen atoms are attached to the same carbon atom,
a is 1 or 2,
b is 0, 1 or 2, and,
if a is 1,
$R_{18}$ is hydrogen, $C_1$–$C_{25}$alkyl, hydroxyl-substituted $C_2$–$C_{24}$alkyl, oxygen- or sulfur-interrupted $C_3$–$C_{25}$alkyl; unsubstituted or $C_1$–$C_4$alkyl-substituted phenyl; $C_7$–$C_9$phenylalkyl which is unsubstituted or is substituted on the phenyl ring by $C_1$–$C_4$alkyl; $C_3$–$C_{24}$alkenyl,

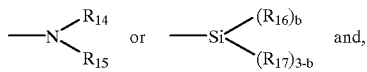 and, and,
if a is 2,
$R_{18}$ is

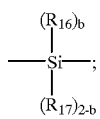

and with the proviso that the compound of the formula II is not ammonia, triethanolamine or ethylamine; or
iii) zirconium, bismuth or calcium.

Preferred groups of novel salts correspond to the preferences expressed above for the coating compositions.

Preference is given, moreover, to salts derived from i) a compound of the formula I" and ii) an amine of the formula II or iii) zirconium, bismuth or calcium in which
R"$_1$ is $C_8$–$C_{14}$alkyl, hydroxyl- or carboxyl-substituted $C_5$–$C_{14}$alkenyl, or $C_8$–$C_{12}$alkenyl, or R"$_1$ and R"$_5$, together with the nitrogen atom to which they are attached, form an oxygen- or sulfur-interrupted 6-membered heterocyclic ring;
$R_2$ and $R_3$ independently of one another are hydrogen, $C_1$–$C_4$alkyl, cyclohexyl, phenyl or benzyl,
R"$_4$ is hydrogen or hydroxyl,
R"$_5$ is $C_8$–$C_{14}$alkyl, $C_5$–$C_{20}$alkenyl or

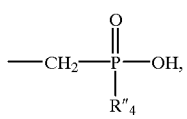

m is 0,
$R_{14}$ and $R_{15}$ independently of one another are hydrogen, $C_1$–$C_{12}$alkyl, hydroxyl-substituted $C_2$–$C_{12}$alkyl, oxygen- or sulfur-interrupted $C_3$–$C_{12}$alkyl; benzyl, $C_3$–$C_{12}$alkenyl or

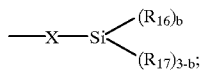

or $R_{14}$ and $R_{15}$, together with the nitrogen atom to which they are attached, form an oxygen- or sulfur-interrupted 6-membered heterocyclic ring;
$R_{16}$ is $C_1$–$C_{12}$alkyl, oxygen- or sulfur-interrupted $C_2$–$C_{12}$alkyl; hydroxyl, $C_1$–$C_{12}$alkoxy or $C_2$–$C_{12}$alkenyl,
$R_{17}$ is hydroxyl or $C_1$–$C_{12}$alkoxy; and, if b is 0, three radicals $R_{17}$ together are $N(CH_2CH_2O—)_3$,
X is a direct bond, $C_1$–$C_8$alkylene, cyclohexylene, phenylene, naphthylene, or oxygen-interrupted $C_4$–$C_{12}$alkylene, with the proviso that never two nitrogen atoms are attached to the same carbon atom,
a is 1 or 2,
b is 0, 1 or 2, and,
if a is 1,
$R_{18}$ is hydrogen, $C_1$–$C_{12}$alkyl, hydroxyl-substituted $C_2$–$C_{12}$alkyl, oxygen-interrupted $C_3$–$C_{12}$alkyl; phenyl, benzyl, $C_3$–$C_{12}$alkenyl or

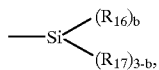

and
if a is 2,
$R_{18}$ is

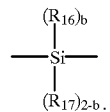

Also of interest are salts derived from i) a compound of the formula I" and ii) an amine of the formula II or iii) zirconium, bismuth or calcium in which
R"$_1$ is $C_8$–$C_{14}$alkyl, or hydroxyl- or carboxyl-substituted $C_5$–$C_{11}$alkyl;
$R_2$ is hydrogen,
$R_3$ is hydrogen,
R"$_4$ is hydrogen or hydroxyl,
R"$_5$ is $C_8$–$C_{14}$alkyl or

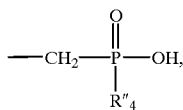

m is 0,
$R_{14}$ and $R_{15}$ independently of one another are hydrogen, $C_1$–$C_4$alkyl, or hydroxyl-substituted $C_2$–$C_4$alkyl; or $R_{14}$ and $R_{15}$, together with the nitrogen atom to which they are attached, form an oxygen-interrupted 6-membered heterocyclic ring,
X is a direct bond,
a is 1, and $R_{18}$ is $C_{14}$alkyl, or hydroxyl-substituted $C_2C_4$alkyl; or is phenyl.

The novel amine salts are of good solubility in water (>1 g/litre at 25° C.), and the novel zirconium, bismuth and calcium salts are poorly water-soluble (<<1 g/Litre at 25° C.).

The salts are expediently prepared by reacting a compound of the formula I' or I" with an amine of the formula II or, respectively, with a zirconium, bismuth or calcium compound.

Preferably, equimolar amounts of the compounds of the formula I' or I" and amines of the formula II are mixed with one another in a temperature range from 10 to 80° C., in particular from room temperature to 60° C., as they are or in a dipolar aprotic solvent, for example dichloromethane, or in a protic solvent, for example ethanol, and are reacted. Where the compound of the formula I' or I" possesses two or more acid groups in the molecule, then one equivalent of the amine of the formula II is employed for each individual acid group.

Some of the compounds of the formula I' or I" are known in the literature; otherwise, they can be prepared in analogy to GB-A-2 121 419; K. Moedritzer et al., J. Org. Chem. 31, 1603–1607 (1966); Houben-Weyl, Methoden der Organischen Chemie [Methods of Organic Chemistry], volume XII/1, pages 483–489 (1963); or volume E2, 302–304 (1982).

Some of the amine oxides of the compounds of the formula I, I' or I", in which m is 1, are known and can be prepared in a known manner, for example by oxidizing the corresponding tertiary amines with an appropriate oxidizing agent, such as a peroxide compound, for example hydrogen peroxide, sodium peroxide, percarbonates, perborates, persulfates, peracids. The oxidation procedure is normally carried out in an aqueous medium [see e.g. Hoh et al. "Hydrogen Peroxide Oxidation of Tertiary Amines", The Journal of the American Oil Chemists' Society, Vol. LV, No. 7, p. 268–271 (July 1963)].

The zirconium, bismuth and calcium salts of compounds of the formula I' or I" can be prepared in a manner known per se. Preferably, a compound of the formula I' or I" is reacted with a zirconium, bismuth or calcium compound. Also of particular interest is the reaction of an alkali metal salt, especially a sodium salt, of the compound of formula I' or I" with a zirconium, bismuth or calcium compound.

As zirconium, bismuth or calcium compound it is expedient to employ an organic zirconium, bismuth or calcium compound or an inorganic zirconium, bismuth or calcium compound.

Examples of organic zirconium, bismuth or calcium compounds are, in particular, alcoholates, for example zirconium n-propoxide, zirconium isopropoxide, zirconium n-butoxide, bismuth n-propoxide; bismutthisopropoxide; or carboxylates for example acetate's especially zirconium acetate.

Examples of inorganic zirconium, bismuth or calcium compounds are halides, especially chlorides, nitrates, carbonates, hydroxides and sulfates. Zirconium carbonate, zirconium sulfate, zirconium oxide chloride, zirconium hydroxide, bismuth carbonate, bismuth sulfate, bismuth hydroxide and calcium carbonate are particularly advantageous.

The zirconium and bismuth salts of compounds of the formula I' or I" can also be referred to as zirconium and bismuth complexes.

In the preparation of zirconium, bismuth or calcium salts starting from compounds of the formula I' or I" and inorganic zirconium, bismuth or calcium compounds, such as, for example, zirconium carbonate, reaction is preferably carried out in water at elevated temperature, in particular at temperatures from 50 to 100° C.

Reaction also takes place in a mixture of organic solvent with water. Particularly preferred mixtures are those of water with aromatic hydrocarbons, such as toluene or xylene, for example, or alcohols, for example methanol, ethanol, n-propanol, isopropanol, n-butanol or 2-butanol. Particular preference is given to toluene, ethanol and 2-butanol. The ratio of water to organic solvent can be varied as desired. Preference is given to a solvent ratio, for example, of water to toluene or water to alcohol (volume:volume) of from 1:10 to 10:1, in particular from 1:5 to 5:1, for example from 1:2 to 2:1.

When using organic zirconium or bismuth compounds such as, for example, zirconium n-propoxide, it is preferred to operate in an anhydrous organic solvent. Suitable organic solvents are all those which are chemically inert towards bases under the reaction conditions. Preference is given to aromatic hydrocarbons such as, for example, toluene or xylene; to aliphatic hydrocarbons such as, for example, pentane, hexane, heptane or octane and their isomer mixtures; to halogenated hydrocarbons such as, for example, di- or trifluoromethane or 1,2-dichloroethane; to ethers such as, for example, diethyl ether, dibutyl ether, 1,4-dioxane or tetrahydrofuran; and to acetonitrile, dimethylformamide, dimethyl sulfoxide or N-methylpyrrolidone.

In the preparation of zirconium or bismuth salts starting from compounds of the formula I' or I" and organic zirconium or bismuth compounds, the reaction is preferably carried out in toluene at elevated temperature, in particular at temperatures from 30 to 80° C.

The hydrolysis of the zirconium and bismuth complexes of compounds of the formula I' or I", prepared from the organic zirconium and bismuth compounds and the compounds of the formula I' or I", is expediently carried out as a suspension in water. The products are preferably isolated by filtering the reaction mixture and then drying the residue at room temperature under a high vacuum.

The reaction of alkali metal salts of compounds of the formula I' or I", especially sodium salts, with inorganic zirconium, bismuth or calcium compounds, for example zirconium sulfate, to give the zirconium, bismuth or calcium salts of compounds of the formula I' or I" is preferably carried out in a solvent, for example water, or in a mixture of water and an organic solvent at room temperature. The products are preferably isolated by filtering the reaction mixture and then drying the residue at room temperature under a high vacuum.

The alkali metal salts of compounds of the formula I' or I" can also be prepared in situ from the corresponding compound of the formula I' or I" with one equivalent of dilute alkali metal hydroxide solution.

With respect to the zirconium or bismuth compound employed the compounds of the formula I' or I" can be used in excess, in equimolar amounts, or in deficit amounts. The molar ratio of the compound of the formula I' or I' to the zirconium or bismuth compound can be from 20:1 to 1:10. Preference is given to a ratio of from 10:1 to 1:3.

The present invention therefore also relates to a process for preparing the novel zirconium and bismuth salts, wherein the molar ratio of the compound of the formula I' or I" to the zirconium or bismuth compound is from 20:1 to 1:10.

The present invention additionally relates to a coating composition comprising a) an organic film-forming binder and b) as corrosion inhibitor at least one zirconium or bismuth complex, obtainable by reacting a compound of the formula I' or I" or an alkali metal salt thereof with a zirconium or bismuth compound, where the molar ratio of the compound of the formula I" or I' to the zirconium or bismuth compound is from 20:1 to 1:10, in particular from 10:1 to 1:5, for example from. 5:1 to 1:3.

The novel salts of compounds of the formula I' or I" can also be complexed with free acid (formula I' or I"), with water or with other anions, such as hydroxides, which are present in the reaction medium. In the case of zirconium acetates or zirconium alkoxides, the acetate anions or the alkoxide anions may be present in the zirconium complexes of compounds of the formula I' or I".

On the basis of the comments made above, the percentage metal content by weight in the zirconium or bismuth complexes of the compounds of the formula I' or I" can be different. Preferred complexes have a metal content of from 5 to 50% by weight, preferably from 5 to 45% by weight, for example from 5 to 40% by weight.

The structures of the zirconium and bismuth salts of compounds of the formula I' or I" can be varied depending on the method of preparation and on the molar ratios of the compounds of the formula I' or I" and zirconium or bismuth compounds that are employed.

The present invention therefore also relates to products obtainable by reacting a compound of the formula I' or I" or an alkali metal salt thereof with a zirconium or bismuth compound.

The examples which follow illustrate the invention in more detail. Parts and percentages are by weight.

EXAMPLE 1 n-Octadecylaminobismethylenephosphonic Acid, Salt with Two Equivalents of N-ethylmorpholine 5.49 g (0.012 mol) of n-octadecylaminobismethylenephosphonic acid are mixed at room temperature with 2.85 g (0.024 mol) of N-ethylmorpholine. This gives 8.17 g (98%) of the dibasic Nethylmorpholine salt of n-octadecylaminobismethylenephosphonic acid as a white powder. Analysis found: C 56.1%; H 10.4%; N 5.9%. Analysis calculated: C 55.9%; H 10.4%; N 6.1%.

EXAMPLE 2

Dihexylaminomethylenephosphonic Acid, Salt with Two Equivalents of N-ethylmorpholine Following the procedure of Example 1, 3.35 g (0.012 mol) of dihexylaminomethylenephosphonic acid and 2.85 g (0.024 mol) of N-ethylmorpholine give 5.92 g (96%) of the dibasic N-ethylmorpholine salt of dihexylaminomethylenephosphonic acid as a brown powder.

EXAMPLE 3

Dioctylaminomethylenephosphonic Acid, Salt with Two Equivalents of N-ethylmorpholine Following the procedure of Example 1, 5.03 g (0.015 mol) of dioctylaminomethylenephosphonic acid and 3.56 g (0.03 mol) of N-ethylmorpholine give 8.43 g (98%) of the dibasic N-ethylmorpholine salt of dioctylaminomethylenephosphonic acid as a brown powder. Analysis found: C 58.7%; H 10.9%; N 6.6%. Analysis calculated: C 58.6%; H 11.4%; N 7.4%.

EXAMPLE 4

2-Ethylhexylaminobismethylenephosphonic Acid, Salt with Two Equivalents N-ethylmorpholine Following the procedure of Example 1, 5.08 g (0.016 mol) of 2-ethylhexylaminobismethyenephosphonic acid and 3.8 g (0.032 mol) of N-ethylmorpholine give 8.77 g (99%) of the dibasic N-ethylmorpholine salt of 2-ethylhexylaminobismethylenephosphonic acid as a white powder. Analysis found: C 46.2%, H 9.1%; N 7.2%. Analysis calculated: C 46.3%; H 9.4%; N 7.7%.

EXAMPLE 5 n-Hexadecylaminobismethylenephosphonic Acid, Salt with Two Equivalents of N-ethylmorpholine Following the procedure of Example 1, 5.15 g (0.012 mol) of N-hexadecylaminobismethyenephosphonic acid and 2.85 g (0.024 mol) of N-ethylmorpholine give 7.93 g (99%) of the dibasic N-ethylmorpholine salt of n-Hexadecylaminobismethylenephosphonic acid as a white powder. Analysis found: C 54.5%; H 10.3%; N 6.0%. Analysis calculated: C 54.6%; H 10.2%; N 6.4%.

EXAMPLE 6 n-Tetradecylaminobismethylenephosphonic Acid, Salt with Two Equivalents of N-ethylmorpholine Following the procedure of Example 1, 6.02 g (0.015 mol) of n-tetradecylaminobismethyenephosphonic acid and 3.56 g (0,03 mol) N-ethylmorpholine give 9.4 g (98%) of the dibasic N-ethylmorpholine salt of n-tetradecylaminobismethylenephosphonic acid as a white powder. Analysis found: C 53.2%; H 10.2%; N 6.3%. Analysis calculated: C 53.2%; H 10.1%; N 6.7%.

EXAMPLE 7 n-Dodecylaminobismethylenephosphonic Acid, Salt with Two Equivalents of N-ethylmorpholine Following the procedure of Example 1, 10 g (0.027 mol) of n-dodecylaminobismethylenephosphonic acid and 6.36 g of (0.054 mol) of N-ethylmorpholine give 16.2 g (99%) of the dibasic N-ethylmorpholine salt of n-dodecylaminobismethylenephosphonic acid as a white powder. Analysis found: C 52.2%; H 10,1%; N 6.7%. Analysis calculated: C 51.7%; H 9.8%; N 7.0%.

EXAMPLE 8 n-Decylaminobismethylenephosphonic Acid, Salt with Two Equivalents of N-ethylmorpholine Following the procedure of Example 1, 5.18 g (0.015 mol) of ndecylaminobismethylene-phosphonic acid and 3.56 g (0.03 mol) of N-ethylmorpholine give 8.67 g (99%) of the dibasic N-ethylmorpholine salt of n-decylaminobismethylenephosphonic acid as a white powder. Analysis found: C 47.6%; H 9.3%; N 6.8%. Analysis calculated: C 50.1%; H 9.6%; N 7.3%.

EXAMPLE 9 n-Octylaminobismethylenephosphonic Acid, Salt with Two Equivalents of N-ethylmorpholine Following the procedure of Example 1, 3.81 g (0.012 mol) of nctylaminoismethylenephosphonic acid and 2.85 g (0.024 mol) of N-ethylmorpholine give 6.51 g (98%) of the dibasic N-ethylmorpholine salt of n-octylaminobismethylenephosphonic acid as a white powder.

EXAMPLE 10 n-Hexylaminobismethylenephosphonic Acid, Salt with Two Equivalents of N-ethylmorpholine Following the procedure of Example 1, 2.89 g (0.01 mol) of n-hexylamino-bismethylenephosphonic acid and 2.38 g (0.02 mol) of N-ethylmorpholine give 5.24 g (99%) of the dibasic N-ethylmorpholine salt of n-hexylaminobismethylenephosphonic acid as a white powder.

EXAMPLE 11 n-Dodecylaminobismethylenephosphonic Acid, Salt with One Equivalent of N,N-dimethylaniline To a suspension of 4.85 g (0.013 mol) of n-dodecylaminobismethylenephosphonic acid in 35 ml of dichloromethane there are added 1.58 g (0.013 mol) of N,N-dimethylaniline; the mixture is stirred at room temperature for one hour and then the dichloromethane is distilled off on a rotary evaporator, to give 6.46 g of the monobasic N,N-dimethylaniline salt of n-dodecylaminobismethylenephosphonic acid as a white powder. Analysis found: C 51.8%; H 8.9%; N 5.3%. Analysis calculated: C 53.4%; H 9.0%; N 5.7%.

EXAMPLE 12 n-Dodecylaminobismethylenephosphonic Acid, Salt with One Equivalent of N-ethylmorpholine Following the procedure of Example 11, 4.85 g (0.013 mol) of n-dodecylaminobismethylenephosphonic acid and 1.54 g (0.013 mol) of N-ethylmorpholine give 6.41 g of the monobasic N-ethylmorpholine salt of n-dodecylaminobismethylenephosphonic acid as a white powder. Analysis found: C 47.8%; H 9.7%; N 5.5%. Analysis calculated: C 49.2%; H 9.5%; N 5.7%.

EXAMPLE 13 n-Dodecylaminobismethylenephosphonic Acid, Salt with Three Equivalents of N-ethylmorpholine Following the procedure of Example 11, 7.46 g (0.02 mol) of n-dodecylaminobismethylenephosphonic acid and 6.91 g (0.06 mol) of N-ethylmorpholine give 15.27 g of the tribasic N-ethylmorpholine salt of n-dodecylaminobismethylenephosphonic acid as a beige resin.

EXAMPLE 14 n-Dodecylaminobismethylenephosphonic Acid, Salt with One Equivalent of Triethanolamine Following the procedure of Example 11, 4.85 g (0.013 mol) of n-dodecylaminobismethylenephosphonic acid and 1.94 g (0.013 mol) of triethanolamine give 6.87 g of the monobasic triethanolamine salt of n-dodecylaminobismethylenephosphonic acid as a white powder. Analysis found: C 45.7%; H 9.5%; N 5.5%. Analysis calculated C 46.0%; H 9.3%; N 5.4%.

EXAMPLE 15 n-Dodecylaminobismethylenephosphonic Acid, Salt with One Equivalent of Triethylamine Following the procedure of Example 11, 4.85 g (0.013 mol) of n-dodecylaminobismethylenephosphonic acid and 1.32 g (0.013 mol) of triethylamine give 6.26 g of the monobasic triethylamine salt of n-dodecylaminobismethylenephosphonic acid as a white powder. Analysis found: C 49.5%; H 10.5%; N 5.6%. Analysis calculated: C 50.6%; H 10.2%; N 5.9%.

EXAMPLE 16 n-Dodecylaminobismethylenephosphonic Acid, Salt with Two Equivalents of Triethanolamine Following the procedure of Example 11, 4.85 g (0.013 mol) of n-dodecylaminobismethylenephosphonic acid and 3.88 g (0.026 mol) of triethanolamine give 8.89 g of the dibasic triethanolamine salt of n-dodecylaminobismethylenephosphonic acid as a white powder. Analysis found: C 45.0%; H 10.1%; N 6.0%. Analysis calculated: C 46.5%; H 9.5%; N 6.3%.

EXAMPLE 17 n-Decylaminobismethylenephosphonic Acid, Salt with Two Equivalents of Triethanolamine Following the procedure of Example 11, 2.41 g (0.007 mol) of n-decylaminobismethylenephosphonic acid and 2.08 g (0.014 mol) of triethanolamine give 3.5 g (78%) of the dibasic triethanolamine salt of n-decylaminobismethylenephosphonic acid as a white powder. Analysis found: C 43.7%; H 9.1%; N 6.1%. Analysis calculated: C 44.8%; H 9.2%; N 6.5%.

EXAMPLE 18 n-Octylaminobismethylenephosphonic Acid, Salt with Two Equivalents of Triethanolamine Following the procedure of Example 11, 2.22 g (0.007 mol) of n-octylaminobismethylenephosphonic acid and 2.08 g (0.014 mol) triethanolamine give 3.3 g (77%) of the dibasic triethanolamine salt of n-octylaminobismethylenephosphonic acid as a white powder. Analysis found: C 42.4%; H 8.9%; N 6.4%. Analysis calculated: C 42.9%; H 9.0%; N 6.8%.

EXAMPLE 19 n-Hexylaminobismethylenephosphonic Acid, Salt with Two Equivalents of Triethanolamine Following the procedure of Example 11, 2.89 g (0.01 mol) of n-hexylaminobismethylenephosphonic acid and 2.98 g (0.02 mol) of triethanolamine give 3.5 g (60%) of the dibasic triethanolamine salt of n-hexylaminobismethylenephosphonic acid as a white resin. Analysis found: C 40.5%; H 8.8%; N 7.1%. Analysis calculated: C 40.9%; H 8.8%; N 7.2%.

EXAMPLE 20 n-Dodecylaminobismethylenephosphonous Acid, Salt with Two Equivalents of N-ethylmorpholine a) 16.2 g (0.2 mol) of aqueous formaldehyde solution (37%) receive, added in portions, first 18.54 g (0.1 mol) of n-dodecylamine and then 26.4 g (0.2 mol) of hypophosphorous acid (aqueous solution 50%). The mixture is then stirred at 25° C. for one hour. After filtration and drying of the filter residue in a vacuum oven at 50° C, 39.4g (54%) of n-dodecyaminobismethylenephosphonous acid are obtained as a beige solid. Analysis calculated: C 49.3%; H 9.7%; N 4.1%. Analysis found: C 47.4%; H 9.9%; N 4.0%.

b) 3.41 g (0.01 mol) of n-dodecylaminobismethylenephosphonous acid as in Example 20a are admixed at room temperature with 2.3 g (0.02 mol) of N-ethylmorpholine. This gives the dibasic N-ethylmorpholine salt of n-dodecylaminobismethylenephosphonous acid. Analysis calculated: C 54.6%; H 10.4%; N 7.4%. Analysis found: C 52.9%; H 10.9%; N 7.1%

EXAMPLE 21 n-Dodecylaminobismethylenephosphonic Acid, Zirconium Complex

A suspension of 18.67 g (0.05 mol) n-dodecylaminobismethylenephosphonic acid and 14.14 g (0.05 mol) of basic zirconium carbonate (zirconium content: 32.25%) in a mixture of 200 ml of water and 20 ml of ethanol is heated to 90° C. with stirring and held at this temperature for one hour. After cooling to 25° C., it is filtered and the filter residue is dried in a vacuum oven at 50° C., to give 25.9 g of the zirconium complex of n-dodecylaminobismethylenephosphonic acid as a white powder. Analysis found: C 31.4%; H 6.8%; N 2.3%; Zr 31.3%.

EXAMPLE 22 n-Dodecylaminobismethylenephosphonic Acid, Calcium Salt

A suspension of 3.73 g (0.01 mol) of n-dodecylaminobismethylenephosphonic acid and 1.0 g (0.01 mol) of calcium carbonate in 15 ml of water is heated to 90° C. and held at this temperature for 2.4 hours. After cooling to 25° C., it is filtered and the filter residue is dried using a vacuum pump. This gives 4.09 g (99%) of the calcium salt of n-dodecylaminobismethylenephosphonic acid as a white powder. Analysis calculated: C 40.9%; H 7.6%; N 3.4%. Analysis found: C 41.0%; H 7.6%; N 3.3%.

EXAMPLE 23

5-Hydroxypentylaminobismethylenephosphonic Acid

To a solution of 36.1 g (0.35 mol) of 5-aminopentanol in 25 ml of water there are added, with ice cooling, stirring and in succession, 82.8 g (0.84 mol) of hydrochloric acid (37% in water) and a solution of 57.4 g (0.7 mol) of phosphorous acid in 45 ml of water. Following the addition of 120.1 g (1.4 mol) of formaldehyde (35% in water), the mixture is heated to 85° C. and held at this temperature for three hours. To isolate the product, the oil obtained following concentration on a rotary evaporator is recrystallized while still hot from an ethanol water mixture. For purification, the resulting white powder is recrystallized three times while still hot from a methanol/water mixture, to give 35.3 g (34.6%) of 5-hydroxypentylaminobismethylenephosphonic acid as a white powder. Analysis calculated for $C_7H_{19}NP_2O_7$: C 28.9%; H 6.6%, N 4.8%. Analysis found: C 28.9%; H 6.7%; N 4.6%.

EXAMPLE 24

12-[Bis(phosphonomethyl)amino]dodecanoic Acid, Salt with Two Equivalents of N-ethylmorpholine 4.43 g (0.011 mol) of 12-[bis(phosphonomethyl)amino] dodecanoic acid are mixed with 2.53 g (0.022 mol) of N-ethylmorpholine. This gives the salt of 12-[bis (phosphonomethyl)-amino]dodecanoic acid with two equivalents of N-ethylmorpholine as a beige powder. Analysis calculated for $C_{26}H_{57}N_3O_{10}P_2$: C 49.3%; H 9.1%; N 6.6%. Analysis found: C 47.5%; H 8.9%; N 6.1%.

EXAMPLE 25

Testing of the Salts in a Coating Formulation

In order to prepare the coating formulation (acrylic dispersion based on Maincote HG-54), components 1 to 8 (formulation without amine salt) and components 1 to 9 (formulation comprising an amine salt) are employed in the sequence stated (see Table 1).

TABLE 1

| Acrylic dispersion based on Maincote HG-54 | | |
|---|---|---|
| | Composition | % by weight |
| 1) | Deion. water | 3.10 |
| 2) | Methylcarbitol[a] | 5.00 |
| 3) | Orotan 165[b] | 0.82 |
| 4) | Triton CF 10[c] | 0.29 |
| 5) | Drew Plus TS 4380[d] | 0.28 |
| 6) | Acrysol RM 8[e] | 0.60 |
| 7) | Bayferrox 130 M[f] | 5.72 |
| 8) | Millicarb[g] | 17.40 |
| 9) | Novel corrosion inhibitor as in Examples 1 to 24 | |
| 10) | Butyldiglycol | 3.67 |
| 11) | Maincote HG-54[h] (41.5% Supply form) | 58.70 |
| 12) | Texanol[i] | 1.50 |
| 13) | Dibutyl phthalate[k] | 1.50 |
| 14) | Sodium nitrite[l] (13.8% in dem. water) | 0.80 |
| 15) | Drew T 4310[m] | 0.32 |
| 16) | Ammonia solution (25%) | 0.30 |
| Total | | 100.00 |

[a]Methylcarbitol ®: Diethylene glycol monomethyl ether (Union Carbide);
[b]Orotan ® 165: dispersion auxiliary (Rohm and Haas Company);
[c]Triton ® CF 10: nonionic wetting agent (Rohm and Haas Comp.);
[d]Drew Plus ® TS 4380: antifoam (Drew Chem. Corp.)
[e]Acrysol ® RM 8: nonionic thickener (Rohm and Haas Comp.);
[f]Bayferrox ® 130 M: iron oxide red (Bayer AG);
[g]Millicarb ®: calcium carbonate (Omya);
[h]Maincote ® HG-54: acrylic dispersion (Rohm and Haas Comp.);
[i]Texanol. ® Coalescent (Eastman Chem. Prod., Inc.);
[k]dibutyl phthalate: plasticizer (Eastman Chem. Prod., Inc.);
[l]sodium nitrite: flash rust inhibitor (Fluka);
[m]Drew ® T 4310: nonionic antifoam (Drew Chem. Corp.).

Components 1 to 8 or 1 to 9 are dispersed using a high-speed stirrer at 3000 revolutions/minute to a degree of ground fineness or ground particulate nature of <15 μm. The outcome of dispersing the pigment paste thus obtained is assessed by determining the grindometer value (ISO 1524). The amount of the novel salts employed is based on the overall solids content of the formulation without salt (overall solids content 47%). Accordingly, an addition of, say, 1.0% of amine salt to 100 g of dispersion denotes, for example, an amount of 0.47 g. To complete the coating formulation, components 10 to 16 of Table 1 are added at a reduced stirring speed (1000 revolutions/minute) in the stated sequence. Subsequently, the pH of the formulation is checked and, if appropriate, is adjusted prior to application to a value of from 8 to 8.5 using ammonia solution (25% strength).

The coating formulation can be applied in undiluted form by airless spraying, spreading or rolling, or, after dilution, by means of conventional spraying. Dilution to the desired spray viscosity is accomplished by adding butyl glycov/water (1:1 w/w).

The coating formulations are applied to steel panels (19×10.5 cm) of the Bonder type (cold-rolled degreased steel; manufactured by Chemetall, Frankfurt am Main/Germany) in a coat thickness which after drying amounts to 50–55 μm. Drying conditions: 10 days at room temperature.

Prior to the beginning of weathering, the "coating films" undergo defined damage in the form of a parallel cut (i.e. parallel to the longest panel edge) using a Bonder cross-cut instrument (Mod. 205; manufactured and sold by Lau, 5870 Hemer/Germany). The panel edges are protected by applying an edge protector (Icosit® 255; manufactured by Inertol AG, Winterthur/Switzerland).

The samples are subsequently subjected to accelerated weathering in a salt spray test in accordance with DIN 50 021 SS for 168 hours (Table 2) or to a humidity test in accordance with ASTM D 4585–87 for 330 hours (Table 3). The assessment of the results is based on the relevant DIN standards in accordance with an evaluation key, by the indication of a corrosion protection value CPF (Corrosion Protection Factor). The CPF is an additive term composed of an assessment of the coating (film) and an assessment of visible underfilm corrosion and appearance of the metal surface, and has a maximum of 12 points. The individual maximum values are 6 points each. The greater the CPF, the better the protection against corrosion.

As additional assessment criteria, the "subfilm migration in the wet state" (cathodic delamination) along the artificial damage side is determined, after the end of the salt spray test, in accordance with DIN 53 167. The lesser the delamination, the more effective the corrosion inhibitor tested. After the end of the humidity test, the wet adhesion of the coating formulation is determined in accordance with DIN 53 151 by making a crosshatch cut followed by the tape tearoff test. According to DIN 53 151 (scale from Gt 0 to Gt 5) a crosshatch value of Gt 0 corresponds to completely intact adhesion of the coating film, whereas Gt 5 corresponds to inadequate adhesion.

TABLE 2

Salt spray test, 168 hours, coat thickness 50 to 55 μm

| Corrosion inhibitor | CPF film | CPF metal | CPF | Cathodic delamination (mm total) |
|---|---|---|---|---|
| — | 3.2 | 3.0 | 6.2 | 90 |
| 1% Example 1 | 6.0 | 5.0 | 11.0 | 28 |
| 2% Example 1 | 6.0 | 5.2 | 11.2 | 30 |
| 1% Example 2 | 4.2 | 5.2 | 9.4 | 14 |
| 1% Example 3 | 4.0 | 4.0 | 8.0 | 16 |
| 1% Example 4 | 5.0 | 5.0 | 10.0 | 22 |
| 1% Example 5 | 5.2 | 5.0 | 10.2 | 26 |
| 1% Example 6 | 5.4 | 5.0 | 10.2 | 18 |
| 1% Example 7 | 5.4 | 5.6 | 11.0 | 16 |
| 1% Example 8 | 5.2 | 5.4 | 10.6 | 12 |
| 2% Example 8 | 5.2 | 5.2 | 10.4 | 10 |
| 1% Example 9 | 5.6 | 5.4 | 11.0 | 12 |
| 1% Example 10 | 4.6 | 5.4 | 10.0 | 24 |

TABLE 2-continued

Salt spray test, 168 hours, coat thickness 50 to 55 μm

| Corrosion inhibitor | CPF film | CPF metal | CPF | Cathodic delamination (mm total) |
|---|---|---|---|---|
| 1% Example 16 | 4.8 | 4.4 | 9.2 | 16 |
| 1% Example 17 | 5.4 | 5.5 | 10.9 | 16 |

TABLE 3

Humidity test, 330 hours, coat thickness 45 to 50 μm

| Corrosion inhibitor | CPF film | CPF metal | CPF | Wet adhesion (Gt value) |
|---|---|---|---|---|
| — | 2.8 | 2.0 | 4.8 | 5 |
| 1% Example 1 | 4.0 | 4.0 | 8.0 | 0 |
| 2% Example 1 | 5.0 | 4.0 | 9.0 | 0 |
| 1% Example 2 | 4.0 | 4.0 | 8.0 | 0 |
| 1% Example 4 | 4.0 | 2.6 | 6.6 | 0 |
| 2% Example 4 | 5.0 | 4.8 | 9.8 | 0 |
| 1% Example 5 | 4.2 | 5.0 | 9.2 | 0 |
| 1% Example 6 | 4.6 | 5.0 | 9.6 | 0 |
| 2% Example 6 | 5.2 | 4.5 | 9.7 | 0 |
| 1% Example 7 | 5.2 | 3.0 | 8.2 | 0 |
| 2% Example 7 | 6.0 | 4.5 | 10.5 | 0 |
| 1% Example 8 | 5.2 | 4.7 | 9.9 | 0–1 |
| 1% Example 9 | 4.4 | 4.0 | 8.4 | 0 |
| 2% Example 9 | 4.8 | 5.4 | 10.2 | 0 |
| 1% Example 10 | 4.0 | 3.8 | 7.8 | 0 |
| 2% Example 10 | 4.4 | 6.0 | 10.4 | 0 |
| 2% Example 16 | 4.8 | 3.6 | 8.4 | 0 |

What is claimed is:
1. A salt derived from
i) a compound of the formula I″

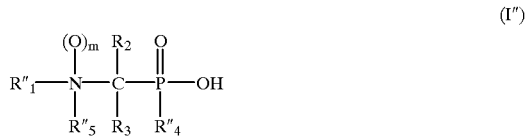

(I″)

in which
R″$_1$ is C$_8$–C$_{14}$alkyl, hydroxyl-, carboxyl- or amino-substituted C$_4$–C$_{14}$alkyl; C$_8$–C$_{14}$alkenyl or

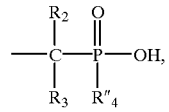

R$_2$ and R$_3$ independently of one another are hydrogen, C$_1$–C$_{20}$alkyl, C$_5$–C$_8$cycloalkyl, unsubstituted or C$_1$–C$_4$alkyl-substituted phenyl; or are benzyl,
R″$_4$ is hydrogen or hydroxyl,
R″$_5$ is hydrogen, C$_8$–C$_{14}$alkyl, C$_2$–C$_{24}$alkenyl or

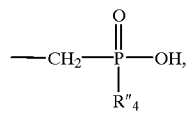

and
m is 0 or 1; with the proviso that, if R″$_1$ or R″$_5$ is hydrogen, m is 0; and ii) an amine of the formula II $$\left[ \begin{array}{c} R_{14} \\ R_{15} \end{array} \!\!\! N\!\!-\!\!X \right]_{\!a}\!\!\!-R_{18} \quad (II)$$

in which
$R_{14}$ and $R_{15}$ independently of one another are hydrogen, $C_1-C_{25}$alkyl hydroxylsubstituted $C_2-C_{24}$alkyl, oxygen- or sulfur-interrupted $C_3-C_{25}$alkyl; $C_7-C_9$phenylalkyl which is unsubstituted or is substituted on the phenyl ring by $C_1-C_4$alkyl; $C_3-C_{24}$alkenyl or $$-\!\!\!-X\!\!-\!\!\mathrm{Si}\!\!<\!\!\!\begin{array}{l}(R_{16})_b \\ (R_{17})_{3-b};\end{array}$$

or $R_{14}$ and $R_{15}$ together with the nitrogen atom to which they are attached, form a 5- or 7-membered heterocyclic ring which is unsubstituted or is substituted by $C_1-C_4$alkyl or is interrupted by oxygen or sulfur, or $R_{14}$ and $R_{15}$, together with the nitrogen atom to which they are attached, form a 6-membered heterocyclic ring which is unsubstituted or is substituted by $C_1-C_4$alkyl and is interrupted by oxygen or sulfur;
$R_7$ is hydrogen or $C_1-C_6$alkyl,
$R_{16}$ is $C_1-C_{25}$alkyl oxygen- or sulfur-interrupted $C_2-C_{25}$alkyl; hydroxyl, $C_1-C_{18}$alkoxy or $C_2-C_{24}$alkenyl,
$R_{17}$ is hydroxyl $C_1-C_{18}$alkoxy, or oxygen- or sulfur-interrupted $C_2-C_{18}$alkoxy; and, if b is 0, three radicals $R_{17}$ together are $N(CH_2CH_2O\!\!-\!\!)_3$,
X is a direct bond, $C_1-C_{18}$alkylene, $C_2-C_{20}$alkylidene, $C_7-C_{20}$phenylalkylidene, $C_5-C_8$-cycloalkylene, unsubstituted or $C_1-C_4$alkyl-substituted phenylene or naphthylene; or $C_4-C_{18}$alkylene which is interrupted by oxygen, sulfur or $$>\!\!\!\!N\!\!-\!\!R_7,$$

with the proviso that never two nitrogen atoms are attached to the same carbon atom,
a is 1 or 2,
b is 0, 1 or 2, and,
if a is 1,
$R_{18}$ is hydrogen, $C_1-C_{25}$alkyl, hydrox-substituted $C_2-C_{24}$alkyl, oxygen- or sulfur-interrupted $C_3-C_{25}$alkyl; unsubstituted or $C_1-C_4$alkyl-substituted phenyl; $C_7C_9$phenylalkyl which is unsubstituted or is substituted on the phenyl ring by $C_1-C_4$alkyl; $C_3-C_{24}$alkenyl, $$-\!\!\!-N\!\!<\!\!\!\begin{array}{l}R_{14} \\ R_{15}\end{array} \quad \text{or} \quad -\!\!\!-\mathrm{Si}\!\!<\!\!\!\begin{array}{l}(R_{16})_b \\ (R_{17})_{3-b}\end{array} \text{and,}$$

if a is 2,
$R_{18}$ is $$-\!\!\!-\!\!\!\begin{array}{c}(R_{16})_b \\ | \\ \mathrm{Si}\!\!-\!\! \\ | \\ (R_{17})_{2-b}\end{array}\!\!\!-;$$

and with the proviso that the compound of the formula II is not ammonia, triethanolamine or ethylamine; or
iii) zirconium, bismuth or calcium, with the proviso that the calcium salt of the compound of the formula A $$N\!\!-\!\!\!\left[\!\!\begin{array}{c}\phantom{x} \\ -C\!\!-\!\!\overset{\overset{\displaystyle O}{\|}}{\underset{\underset{\displaystyle OH}{|}}{P}}\!\!-\!\!OH \\ H_2\end{array}\!\!\right]_{\!3} \quad (A)$$

is excluded.
2. A salt according to claim 1, in which
$R''_1$ is $C_8-C_{14}$alkyl, hydroxyl- or carboxyl-substituted $C_5-C_{14}$alkyl; or is $C_8-C_{12}$alkenyl,
$R_2$ and $R_3$ independently of one another are hydrogen, $C_1-C_4$alkyl, cyclohexyl, phenyl or benzyl,
$R''_4$ is hydrogen or hydroxyl,
$R''_5$ is $C_8-C_{14}$alkyl, $C_5-C_{20}$alkenyl or $$-\!\!\!-CH_2\!\!-\!\!\overset{\overset{\displaystyle O}{\|}}{\underset{\underset{\displaystyle R''_4}{|}}{P}}\!\!-\!\!OH,$$

m is 0,
$R_{14}$ and $R_{15}$ independently of one another are hydrogen, $C_1-C_{12}$alkyl, hydroxyl-substituted $C_2-C_{12}$alkyl, oxygen- or sulfur-interrupted $C_3-C_{12}$alkyl; benzyl, $C_3-C_{12}$alkenyl or $$-\!\!\!-X\!\!-\!\!\mathrm{Si}\!\!<\!\!\!\begin{array}{l}(R_{16})_b \\ (R_{17})_{3-b};\end{array}$$

or $R_{14}$ and $R_{15}$, together with the nitrogen atom to which they are attached, form an oxygen- or sulfur-interrupted 6-membered heterocyclic ring;
$R_{16}$ is $C_1-C_{12}$alkyl, oxygen- or sulfur-interrupted $C_2-C_{12}$alkyl; hydroxyl, $C_1-C_{12}$alkoxy or $C_2-C_{12}$alkenyl,
$R_{17}$ is hydroxyl or $C_1-C_{12}$alkoxy; and, if b is 0, three radicals $R_{17}$ together are $N(CH_2CH_2O\!\!-\!\!)_3$,
X is a direct bond, $C_1-C_8$alkylene, cyclohexylene, phenylene, naphthylene, or oxygen-interrupted $C_4-C_{12}$alkylene, with the proviso that never two nitrogen atoms are attached to the same carbon atom,
a is 1 or 2,
b is 0, 1 or 2, and,
if a is 1,
$R_{18}$ is hydrogen, $C_1-C_{12}$alkyl, hydroxyl-substituted $C_2-C_{12}$alkyl, oxygen-interrupted $C_3-C_{12}$ alkyl; phenyl, benzyl, $C_3-C_{12}$alkenyl or

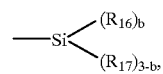

and
if a is 2,
$R_{18}$ is

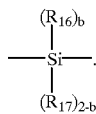

3. A salt according to claim 1, in which
$R''_1$ is $C_8$–$C_{14}$alkyl, or hydroxyl- or carboxyl-substituted $C_5$–$C_{11}$alkyl;
$R_2$ is hydrogen,
$R_3$ is hydrogen,
$R''_4$ is hydrogen or hydroxyl,
$R''_5$ is $C_8$–$C_{14}$alkyl or

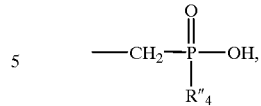

m is 0,
$R_{14}$ and $R_{15}$ independently of one another are hydrogen, $C_1$–$C_4$alkyl, or hydroxyl-substituted $C_2$–$C_4$alkyl; or $R_{14}$ and $R_{15}$, together with the nitrogen atom to which they are attached, form an oxygen-interrupted 6-membered heterocyclic ring,
X is a direct bond,
a is 1, and
$R_{18}$ is $C_1$–$C_4$alkyl, or hydroxyl-substituted $C_2$–$C_4$alkyl; or is phenyl.

* * * * *